United States Patent [19]

Webb et al.

[11] Patent Number: 4,871,661
[45] Date of Patent: * Oct. 3, 1989

[54] PROCESS FOR TESTING THE CARCINOGENICITY OF A MATERIAL OR THE PRESENCE OF CANCER-INDUCING FACTORS IN AN ENVIRONMENT

[75] Inventors: Thomas E. Webb; Dorothy E. Schumm; Margaret Hanausek-Walaszek; Zbigniew Walaszek; Raymond W. Lang, all of Columbus, Ohio

[73] Assignee: The Ohio State University Research Foundation, Columbus, Ohio

[*] Notice: The portion of the term of this patent subsequent to May 24, 2005 has been disclaimed.

[21] Appl. No.: 745,924

[22] Filed: Jun. 18, 1985

Related U.S. Application Data

[63] Continuation-in-part of Ser. No. 554,439, Nov. 23, 1983.

[51] Int. Cl.$^4$ .......................... C12Q 1/00; C12Q 1/02; G01N 33/564; G01N 33/53
[52] U.S. Cl. .......................................... 435/7; 435/29; 530/352; 530/806; 436/507; 436/518; 436/523; 436/536; 436/539; 436/541; 436/598
[58] Field of Search .............. 435/29, 240, 948, 172.1, 435/7, 4; 436/507, 518, 523, 536, 539, 541, 548; 530/350, 387, 806, 352; 514/2, 6, 8; 424/85, 88; 421/85.8

[56] References Cited

U.S. PATENT DOCUMENTS

| | | | |
|---|---|---|---|
| 4,003,789 | 1/1977 | Green | 435/29 |
| 4,066,510 | 1/1978 | Thilly | 435/29 |
| 4,256,832 | 3/1981 | Findl et al. | 435/6 |
| 4,345,026 | 8/1982 | Lew | 435/4 |
| 4,407,942 | 10/1983 | Birnboin | 435/6 |
| 4,594,319 | 1/1986 | Sharma | 435/7 |

FOREIGN PATENT DOCUMENTS

2067286  1/1980  United Kingdom ................. 424/88

OTHER PUBLICATIONS

Hanausek et al., *Cancer Invest* vol. 2 (6) pp. 433–441 1984 "Characterization of a 60,000-Dalton Oncofetal Protein from the Plasma of Tumor-Bearing Rats."

*Primary Examiner*—Robin L. Teskin
*Attorney, Agent, or Firm*—Sidney W. Millard

[57] ABSTRACT

Materials can be screened for carcinogenic properties by administering them to test animals and assaying biological tissue, preferably plasma, for the presence of a 60K cancer-associated phosphoprotein. The test is applicable to a wide range of chemically-diverse carcinogens and is not restricted to carcinogens having one particular mode of action.

19 Claims, No Drawings

PROCESS FOR TESTING THE CARCINOGENICITY OF A MATERIAL OR THE PRESENCE OF CANCER-INDUCING FACTORS IN AN ENVIRONMENT

The United States has certain rights in this invention pursuant to grants CA30267 and P-30-CA-16058-09 by the National Institute of Health.

The application is a continuation-in-part of application Ser. No. 554,439 filed Nov. 23, 1983, now allowed by Thomas E. Webb, Dorothy E. Schumm and Magaret Hanausek-Walaszek.

BACKGROUND OF THE INVENTION

This invention relates to a process for determining the carcinogenicity of a material or the presence of cancer-inducing factors in an environment.

A wide variety of materials, having very diverse chemical natures, are known to be capable of inducing cancer in man and other animals. In some cases, it has been found that materials which have been produced and used on a vast scale for decades have carcinogenic properties, so that millions of people have been exposed to such carcinogens before their carcinogenic nature was discovered. For example, benzene, which is commonly used in industry and in the laboratory as a solvent, has recently been found to be a carcinogen.

Increasing attention is now being paid to detecting carcinogenic properties of materials or environments before substantial numbers of persons are exposed thereto. Unfortunately, testing the carcinogenic character of materials poses a number of formidable problems. Known carcinogens include a large number of chemical compounds and mixtures having a wide variety of chemical structures, and the present state of knowledge as to how carcinogens cause cancer is such that not even experts in the field can estimate with any degree of confidence whether a specific compound will be a carcinogen, and if so, how potent a carcinogen. Consequently, every compound to which a substantial number of persons will be exposed must be tested for its carcinogenic character, and indeed, carcinogen testing tests have already been carried out on tens of thousands of compounds. Testing for carcinogenic character is further hampered by the long incubation periods, which can range from weeks to decades, between exposure to the carcinogen and the onset of the resultant cancer. Furthermore, carcinogens can be absorbed into the body in various ways, for example by mouth, through the lungs, or through the skin, and may cause cancer at a wide variety of different sites, often far removed from the locus at which the carcinogen enters the body. Some carcinogens will only cause cancer at a single site and there is no way of predicting, except in the case of compounds closely related to a known carcinogen at which site a suspected carcinogen under test will produce cancer. Thus, screening of a large number of possible carcinogens frequently involves elaborate dissection of large numbers of test animals, which greatly increases the costs of carcinogen testing.

Futhermore, since one does not know how long the incubation period will be before a carcinogen induces a cancer, it is necessary to minutely examine test animals for very small tumors after varying incubation times, and even skilled workers may miss very small tumors which might indicate carcinogenic character in the material under test.

There is thus a need for a carcinogen screening test which is cheap, can be rapidly applied to a large number of compounds, which will give an indication of the carcinogenic character of the test material regardless of the site at which that material exerts its carcinogenic character, and which does not depend upon elaborate visual inspection of a large number of tissues from test animals to visually detect tumors therein. Moreover, in view of the long incubation periods of many carcinogens, it is highly desirable that such a carcinogen screening test be able to give an indication of carcinogenic properties in a test material before macroscopically-visible tumors appear in the test animals, since this greatly reduces the duration and cost of such a carcinogen screening test. No prior art carcinogen screening test meets all these requirements. In particular, most prior art tests are limited in the variety of tumors which will give a positive indication in the test.

The present invention provides a carcinogen screening test which meets the above requirements.

In the aforementioned parent application Ser. No. 554,439, it is disclosed that a cancer-associated phosphoprotein can be isolated from the plasma of mammals suffering from any of a wide variety of cancers. This cancer-associated phosphoprotein ("cancer marker protein") has the following characteristics:

(a) not being precipitated by 30% saturated aqueous ammonium sulfate solution at 25° C.;

(b) having a molecular weight of approximately 60,000;

(c) being precipitated from aqueous solution by 3.3% streptomycin sulfate;

(d) having substantially no autophosphorylation activity but being phosphorylated with adenosine triphosphate in the presence of an exogenous protein kinase;

(e) having substantially no protein kinase activity;

(f) having the capacity to liberate ribonucleic acid from cell nuclei; and (g) being substantially free of albumin. In addition, unlike previously detected oncofetal proteins, the cancer-associated phosphoprotein is not present in the blood of healthy pregnant females.

The cancer-associated phosphoprotein is prepared by the following procedure:

(a) separating from the plasma of a mammal suffering from cancer the fraction of plasma protein which is not precipitated by 30% saturated aqueous ammonium sulfate solution;

(b) dispersing this fraction of plasma protein in a buffer and dialyzing the resultant protein solution against the buffer;

(c) separating the fraction of the dialyzed protein having a molecular weight of about 60,000; and (d) removing substantially all albumin from the 60,000 molecular weight fraction.

It is further disclosed in the aforementioned application Ser. No. 554,439 (the entire disclosure of which is herein incorporated by reference) that the purified protein preparation prepared in the above manner can be introduced into the bloodstream of a mammal, thereby inducing in the mammal antibodies to the cancer-associated phosphoprotein, and these antibodies can be extracted in conventional ways to yield an antiserum to the cancer-associated phosphoprotein. Alternatively, a monoclonal antibody preparation containing antibodies to the cancer-associated phosphoprotein can be prepared by introducing into the bloodstream of a mouse the purified cancer-associated phosphoprotein preparation, allowing this preparation to remain in the mouse for at least about one day, removing spleen and/or lymph node cells from the mouse, fusing these removed cells with mouse myeloma cells and culturing the resultant hybridoma cells, selecting one or more hybridoma cells capable of producing the desired antibody and harvesting this antibody from the selected cell or cells. The antibody preparation produced by either of these techniques is substantially free of antibodies to normal plasma fraction, is capable of being precipitated by 35% saturated aqueous ammonium sulfate solution and is capable of forming a conjugate with the cancer-associated phosphoprotein. The antibody preparation is capable of forming a visible precipitate with the cancer-associated phosphoprotein when they are diffused towards one another in agar gel but is not capable of forming a conjugate with the 25K protein from human plasma nor the 35K protein fraction from rat plasma.

Finally, the aforementioned application Ser. No. 554,439 discloses that the presence of any of a wide variety of cancers can be detected in mammals by producing an antibody to the form of the cancer-associated phosphoprotein present in cancerous mammals of the appropriate species by the techniques discussed above, contacting these antibodies with biological material, preferably plasma, from the mammal, and detecting the presence of a reaction product between the antibodies and the antigen.

Obviously, this technique can be used to test a mammal for the presence of tumors which have been induced as a result of the exposure of the mammal to a carcinogen. However, it has now been discovered that not only can the test for the presence of the cancer-associated phosphoprotein detect the presence of tumors induced by carcinogens; in addition, this test will give positive results in mammals exposed to a carcinogen before macroscopically visible tumors are present in the mammal. Accordingly, this test provides a basis for a rapid carcinogen screening test.

SUMMARY OF THE INVENTION

Accordingly, this invention provides a process for determining the ability of a material to induce cancer in a test animal, this process comprising administering the material to the test animal and thereafter assaying biological material from the test animal for the presence of a phosphoprotein having the following characteristics:

(a) not being precipitated by 30% saturated aqueous ammonium sulfate solution at 25° C.;

(b) having a molecular weight of approximately 60,000;

(c) being precipitated from aqueous solution by 3.3% streptomycin sulfate;

(d) having substantially no autophosphorylation activity but being phosphorylated with adenosine tryphosphate in the presence of exogenous protein kinase;

(e) having substantially no protein kinase activity;

(f) having the capacity to liberate ribonucleic acid from cell nuclei and (g) not being present in the maternal blood of non-cancerous normal pregnant mammals of the species to which the test animal belongs.

This invention also provides a process for determining the presence of cancer-inducing factors (such as carcinogens, or radiation) in an environment, which process comprises exposing a test animal to said environment and thereafter assaying biological material from the test animal for the aforementioned cancer-associated phosphoprotein.

DETAILED DESCRIPTION OF THE INVENTION

The carcinogenic character of a test material may be determined by the process of the present invention either before or after the test animal receiving the carcinogen or exposed to the environment has macroscopically-visible tumors induced therein by the carcinogen or environment. However, as already indicated, desirably the assay for the cancer-associated phosphoprotein if performed at a time when the test animal is not suffering from cancer, since, given the relative lengthy incubation times of many animals, performing the assay at this pre-cancerous stage greatly reduces the duration, and hence the expense, of the carcinogen screening test. The exact time at which the assay for the cancer-associated phosphoprotein should be performed may vary with the exact experimental protocol employed, and especially with the type of carcinogen or suspected carcinogen being tested. Obviously, if previous test results have been obtained using chemically closely-related test materials, the assay should be performed at a time when the cancer-associated phosphoprotein has been found to be present in animals exposed to the closely-related compounds. When the process of the present invention is performed on compounds not closely related to those previously tested, it may obviously be necessary to perform a series of assays at varies time intervals to allow for possible delay in the induction of the cancer-associated phosphoprotein by the test compound. However, in general it is desirable that the assay be performed at least seven days after the first administration of the test material to the test animal or exposure to the test environment, since induction of significant amounts of the cancer-associated phosphoprotein in the test animal usually takes at least this long. In practice, it has been found that with many carcinogens or environments a period of 21 days from first administration of the carcinogen or exposure to the test environment suffices for induction of significant concentrations of the cancer-associated phosphoprotein in the bloodstream of the test animal and hence performing the assay 21 days after the first administration of the test compound to the test animal appears likely to give good results.

The choice of test animal for use in the process of the present invention is not critical, and is guided by the same considerations as in prior carcinogen screening tests i.e. the similarity between the response of the test animal to carcinogens and the response of the animal (including man) in which the possible carcinogenic activity of the test material is to be determined. We prefer to use mammals, especially the rat, since this mammal is readily available commercially in standard forms and is relatively cheap to house and feed during the tests. Furthermore, we have found that an appropriate antibody to the form of the cancer-associated phosphoprotein produced by the rat can be prepared by standard methods, as set forth in the aforementioned parent application Ser. No. 554,439.

Furthermore, a variety of routes can be used to administer the test material to the test animals in the process of the present invention. As will be apparent to those skilled in the art, desirably the route used to administer the test material should be the same route by which the test material is likely to be introduced into the bodies of the persons or other animals which will come into contact with the test material under practical situations. Thus, the test material may be administered orally, intraperitoneally intravenously, subcutaneously or via the lungs of the test animal.

A variety of biological materials from the test animal may be assayed for the presence of the cancer-associated phosphoprotein in the process of the present invention. For example, if one is screening a test material suspected of causing liver cancer, one might dissect out the livers of the test animals and assay these livers for the presence of the cancer-associated phosphoprotein. However, in general we prefer that the biological material assayed be blood or a blood fraction from the test animal. It has been found that readily detectable levels of the cancer-associated phosphoprotein are present in the blood of test animals exposed to known carcinogens, regardless of the site at which the carcinogen ultimately produces a tumor in the test animals. Moreover, the use of blood as the biological material allows repeated extractions of test material at varying times from the test animals without the need to kill the animals before an appropriate sample of biological material can be taken, and thus reduces the number of animals needed for a test in which samples for assay are taken at varying times.

The preferred blood fraction for assay in the process of the present invention is plasma, since the cancer marker protein is readily concentrated from plasma and separated from the 35K protein, for example by chromatography on Sepharose CL-6B resin, or by the more elaborate process described in the aforementioned parent application Ser. No. 554,439. Such concentration and purification of the cancer-associated phosphoprotein before testing of the biological material naturally increases the sensitivty of the assay. It should be noted that although the cancer-associated phosphoprotein is readily detectable in plasma, serum should not be used as the biological material in the process of the present invention, since the manipulations necessary to separate serum from whole blood destroy the cancer-associated phosphoprotein. Furthermore, if tissues other than blood are to be used as the biological material in the process of the present invention, it should be noted that our results to date indicate that the cancer-associated phosphoprotein is a cytoplasmic protein, not a nuclear protein, so that it is not desirable to use a nuclear or nuclear-enriched fraction of tissue as the biological material in the process of the present invention.

The assay for the cancer-associated phosphoprotein may be effected by any technique capable of detecting this phosphoprotein. For example, the assay may be effected by measuring the RNA-releasing activity of the cancer-associated phosphoprotein, using the method described above and in Example 1 below. However, this RNA-releasing activity measuring method is too cumbersome and complicated to be suitable for routine use by laboratory technicians, as is in practice essential when carcinogen screening tests have to be carried out on large numbers of compounds. Accordingly, it is preferred that the assay be performed immunologically, since immunological methods are capable of routine application by relatively low-level personnel. Thus, preferably the assay is effected by contacting the biological material from a test animal with antibodies to the phosphoprotein, these antibodies not being capable of performing a conjugate with the 25K protein fraction from human plasma nor the 35K protein fraction from rat plasma, and detecting the presence of a reaction product to form a group with the antibodies and the phosphoprotein. The antibodies to the cancer-associated phosphoprotein used in such immunological assay methods can be either polyclonal antibodies (such as those produced by passage of the cancer-associated phosphoprotein through rabbits and concentration of the resulting antibody serum) or monoclonal antibodies.

Although other immunological methods, such as radioimmunoassay, can be used, the simplest form of immunological assay for routine use is an ELISA assay. In an ELISA assay, wells in a tray are first coated with the cancer-associated phosphoprotein, obtained as described in our aforementioned parent application Ser. No. 554,439. Next, an antibody serum specific for the cancer-associated phosphoprotein is mixed with the test sample to be assayed, and the resultant mixture added to the wells already coated with the cancer-associated phosphoprotein. If the test sample contains the cancer-associated phosphoprotein, this protein will bind to the antibody before the mixture is added to the wells, thereby preventing the antibody from binding to the cancer-associated phosphoprotein previously bound to the well. If, however, the test sample does not contain cancer-associated phosphoprotein, then the antibody will bind to the protein bound to the well. Next, the wells are rinsed, thereby washing away any antibody not bound to the phosphoprotein on tee walls of the well. To the well is then added an immunoglobin antibody (the preferred such antibody being goat anti-rabbit IgG antibody) conjugated to horseradish peroxidase. If any bound rabbit antibody is present on the walls of the cell, this conjugate binds to such bound rabbit antibody. The wells are then rinsed to remove any unbound conjugate and a substrate capable of producing a color with the peroxidase enzyme is added to the wells. The color which develops is proportional to the concentration of the bound conjugate. Accordingly, in such an assay the decrease in color of a test sample, as compared to a control in which the test sample contains no cancer-associated phosphoprotein, is proportional to the amount of the cancer-associated phosphoprotein in the sample being tested.

Whatever test protocol is adopted in the process of the present invention, it will usually be desirable to use control animals which are not exposed to the test material or environment. Where the nature of the biological material (e.g., blood or plasma) used in the test permits, it may also be desirable to take samples of the biological material prior to exposing the animals to the test material or environment, in order to ensure that the animals are not already suffering from elevated levels of the cancer-associted phosphoprotein.

The following Examples are now given, though by way of illustration only, to show details of particularly preferred reagents, conditions and techniques used in the process of the present invention.

EXAMPLE I

This Example illustrates a process of the present invention in which the assay for the cancer-associated phosphoprotein is effected by determining the RNA-releasing activity of plasma from the test animal.

Various known carcinogens and non-carcinogens were administered to 50-day old female rats of the Sprague-Dawley strain. The carcinogens were administered at dosage rates known from the literature to be effective in inducing cancer. Except for aflatoxin $B_1$, which was administered intragastrically, all the carcinogens and non-carcinogens were administered intraperitoneally. The nitrosoamines were administered in 0.5ml. of 0.9% saline. The remaining carcinogens were administered in sesame oil. In the case of the non-carcinogens, the caffeine and phenobarbital were administered in saline, the nonadecafluorodecanoicacid was administered in propylene glycol and the remaining non-carcinogens were administered in 0.5ml. of sesame oil. Controls were provided by injecting rats intraperitoneally with the sesame oil vehicle only.

Approximately 21 days after exposure to the test compounds, blood was obtained from the rats under light ether anesthesia by cardiac puncture using heparinized syringes. Following removal of cellular components by centrifugation, the plasma was stored frozen until testing.

To concentrate, and to separate the cancer-associated phosphoprotein form the 35K factor of the plasma prior to testing, a 30–60% ammonium sulfate fraction of the plasma containing 80mg. of protein was applied, after dialysis, in a 50 mM Tris, 25 mM potassium chloride, 2.5 mM magnesium chloride buffer pH 7.5, to a 1.6×90 cm column of Sepharose CL-6B resin and eluted with the same buffer. 3 ml fractions were collected and 200 microliter aliquots were assayed using the RNA-releasing test described above, except that the prelabeling of the nuclei was effected with only 30 microcuries of the radiolabelled orotic acid. The values expressed in Table 1 below were obtained by summing the percent nuclear counts per minute transported in each fraction of the 60K region of the Sepharose CL-6B profile and substracting the units in the corresponding region of the profile of the control rat plasma.

The results obtained are shown in Table I below.

TABLE 1

| Test Compound | RNA-releasing Activity |
| --- | --- |
| Known Carcinogens | |
| 1,2-dimethylhydrazine | 5.71 |
| (560 micromoles/kg.) | |
| N—Nitroso-N,N—dimethylamine | 3.40 |
| (135 micromoles/kg.) | |
| N—Nitroso-N,N—diethylamine | 4.21 |
| (1 millimole/kg.) | |
| N—Nitroso-N,N—dibutylamine | 5.44 |
| (760 micromoles/kg.) | |
| N—Methyl-N—nitrosourea | 4.69 |
| (440 micromoles/kg.) | |
| N—Ethyl-N—nitrosourea | 4.50 |
| (600 micromoles/kg.) | |
| Ethyl carbamate (urethane) | 3.80 |
| (11.2 millimoles/kg.) | |
| 2-Naphthylamine | 3.29 |
| (500 micromoles/kg.) | |
| 2-Acetylaminofluorene | 5.11 |
| (200 micromoles/kg.) | |
| 1-Nitropyrene | 5.30 |
| (105 micromoles/kg.) | |
| Safrole | 5.90 |
| (600 micromoles/kg.) | |
| Benz[a]anthracene | 4.92 |
| (160 micromoles/kg.) | |
| 7,12-Dimethylbenz[a]anthracene | 6.42 |
| (160 micromoles/kg.) | |
| Benzo[a]pyrene | 7.73 |
| (210 micromoles/kg.) | |
| Benzo[e]pyrene | 3.37 |
| (210 micromoles/kg.) | |
| 3-Methylcholanthrene | 5.62 |
| (160 micromoles/kg.) | |
| Aflatoxin $B_1$ | 4.37 |
| (10 micromoles/kg.) | |
| Aflatoxin $G_2$ | 3.80 |

TABLE 1-continued

| Test Compound | RNA-releasing Activity |
| --- | --- |
| (10 micromoles/kg.) | |
| Known non-carcinogens | |
| Dimethylformamide | 1.30 |
| (200 micromoles/kg.) | |
| 1-Naphthylamine | 0.15 |
| (500 micromoles/kg.) | |
| Anthracene | 0.17 |
| (160 micromoles/kg.) | |
| Fluorene | 0.14 |
| (160 micromoles/kg.) | |
| 2-Fluoro-1,12-dimethylbenz[a]anthracene | 0.10 |
| (160 micromoles/kg.) | |
| Naphthalene | 0.12 |
| (1 millimole/kg.) | |
| Pyrene | 0.05 |
| (160 micromoles/kg.) | |
| Acridine | 0.00 |
| (15 micromoles/kg.) | |
| Caffeine | 0.07 |
| (100 micromoles/kg.) | |
| Nonadecafluorodecanoic acid | 0.00 |
| (50 micromoles/kg.) | |
| Phenobarbital | 0.08 |
| (80 micromoles/kg.) | |
| Riboflavin | 0.01 |
| (265 micromoles/kg.) | |
| 2,3,7,8-Tetrachlorodibenzo-p-dioxine(TCDD) | 0.00 |
| (0.125 micromoles/kg.) | |

From Table 1 above, it will be seen that all eighteen known carcinogens induced the presence of substantial amounts of the cancer-associated phosphoprotein in the plasma of the rats. In contrast, none of the thirteen non-carcinogens tested, except dimethylformamide, induced significant quantities of the cancer-associated phosphoprotein in the plasma of the test animals, despite the fact that the non-carcinogens used in these experiments were specifically chosen to be close chemical relative of the tested carcinogens. The one apparent exception to the sharp distinction between carcinogens and non-carcinogens obtained in these experiments, namely dimethylformamide, may be a result of misclassification of dimethylformamide as a non-carcinogen. Although the carcinogenicity of dimethylformamide is uncertain, it does have the ability to reversably induce the differentiation of some types of transformed cells: see Antoine et al., Lack of Mutagenic Activity of Dimethylformamide, Toxicology, 26, 207–212 (1983); and Fontana, et al., Identification of a Population of Bipotent Stem Cells in the HL60 Human Promyeloctytic Leukemia Cell Line, Proc. Natl. Acad. Sci. U.S.A., 78, 3863–3866 (1981).

Thus, the results obtained in these experiments indicate that release of the cancer-associated phosphoprotein into the plasma of the test animals is a reliable guide to the carcinogenicity of the test materials. It should be noted that both nonadecafluorodecanoic acid and 2,3,7,8-tetra-chlorodibenzo-p-dioxine are very potent toxins in the rat, although not carcinogens, and do not induce significant quantities of the cancer-associated phosphoprotein. Furthermore, two of the carcinogens tested, namely urethane and aflatoxin $G_2$ are currently considered to act by epigenetic as opposed to genotoxic mechanisms; thus, release of the cancer-associated phosphoprotein does not seem to be dependent upon the particular mode of action of the carcinogen being tested.

Further experiments indicate that release of the cancer-associated phosphoprotein into the plasma was not induced upon induction of liver regeneration in the rat by partial hepatectomy, nor by acute or chronic treatment of the rats with the non-carcinogenic tumor promoter phenobarbital.

EXAMPLE 2

This example illustrates a process of the present invention in which the assay for the cancer-associated phosphoprotein is effected by means of an ELISA test.

Samples of the purified 60K protein fraction from the Sepharose CL-6B column used in Example 1 above were subjected to an ELISA assay. These purified protein fractions were taken from the rats receiving the carcinogens 1,2-dimethylhydrazine, N-Nitroso-N,N-dibutylamine,2-acetylaminofluorene, 1-nitropyrene and safrole, and from the non-carcinogens caffeine, naphthalene, riboflavin, and acridine, and from two other rats which had received carbon tetrachloride given in the same manner as the other non-carcinogens described in Example 1 above. Also subjected to the same ELISA assay were purified protein fractions from the control rats and from a rat suffering from a hepatoma 7777 tumor.

The ELISA assay was conducted in the following manner. A sample of the cancer-associated phosphoprotein prepared in the manner described in Example 1 of the aforementioned parent application Ser. No. 554,439 was bound to a well in a plastic tray, and the well thereafter washed thoroughly. A polyclonal rabbit antibody serum prepared as described in Example 2 of the aforementioned parent application Ser. No. 554,439 was then mixed with the protein sample to be assayed and the resultant mixture incubated at 37° C. for 30 minutes. The mixture was then added to the well containing the cancer-associated phosphoprotein, and the tray incubated for one hour at 37° C., then washed thoroughly. Following this washing, there was added to the well a goat anti-rabbit IgG antibody serum conjugated to horseradish peroxidase enzyme, and the tray was incubated for one hour at 37° C. then washed thoroughly. The substrate for the horseradish peroxidase enzyme, namely 2,2-azino-di(3-ethylbenzthiazoline sulfonic acid) was added to the well and the tray incubated to 15 minutes at room temperature. The color development was then stopped by addition of a 2 mM solution of sodium azide and the intensity of the color in the wells determined using a spectrophotometer at 410 nM.

To determine the maximum possible optical density, a control test was run in which the test sample was replaced with a buffer containing no cancer-associated phosphoprotein; this optical density represents the maximum possible reaction of uninhibited antibody binding to the bound cancer-associated phosphoprotein. The optical density of a well containing as a sample the standard solution of cancer-associated phosphoprotein used in the first step of the ELISA assay is designated 100% inhibition. The optical density of a well containing as a control sample an equivalent fraction of normal rat plasma free of cancer-associated phosphoprotein is designated 0% inhibition; the optical density of this control sample should be close to that of the sample using the buffer solution The samples tested for the presence of the cancer-associated phosphoprotein are designated positive when the optical density exceeds that of the control value by two standard deviations. The concentration of cancer-associated phosphoprotein is directly related to the percentage inhibition and can be compared to that of the standard solution of the cancer-associated phosphoprotein. The results obtained are shown in Table 2 below.

TABLE 2

| Test Compound | Percentage Inhibition |
| --- | --- |
| Controls | |
| Rat plasma fraction from rat having hepatoma 7777 tumor | 100 |
| Normal rat fraction | 4 |
| Carcinogens | |
| 1,2-dimethylhydrazine | 79 |
| N—nitroso-N,N—dibutylamine | 75 |
| 2-acetylaminofluorene | 87 |
| 1-nitropyrene | 74 |
| Safrole | 80 |
| Non-carcinogens | |
| Caffeine | 14 |
| Naphthalene | 18 |
| Riboflavin | 11 |
| Acridine | 2 |
| Carbon tetrachloride-1 | 1 |
| Carbon tetrachloride-2 | 10 |

From the data in Table 2 above, it will be seen that the ELISA assay distinguished between all the carcinogens and all the non-carcinogens, all the carcinogens having at least 70% inhibition, while none of the non-carcinogens exceeded 20% inhibition.

It will be apparent to those skilled in the art that numerous changes and modifications can be made in the preferred embodiments of the invention described above without departing from the scope of the invention. Accordingly, the whole of the foregoing description is to be construed in an illustrative and not in a limitative sense, the scope of the invention being defined solely by the appended claims.

We claim:

1. A process for determining the ability of a material to induce cancer in a test animal, said process comprising administering said material to said test animal and thereafter assaying biological material from said test animal for the presence of a phosphoprotein having the following characteristics:
   (a) not being precipitated by 30% saturated aqueous ammonium sulfate solution at 25° C.;
   (b) having a molecular weight of approximately 60,000;
   (c) being precipitated from aqueous solution by 3.3% streptomycin sulfate;
   (d) having substantially no autophosphorylation activity but being phosphorylated with adenosine triphosphate in the presence of an exogenous protein kinase;
   (e) having substantially no protein kinase activity;
   (f) having the capacity to liberate ribonucleic acid from cell nuclei; and
   (g) not being present in the maternal blood of non-cancerous normal pregnant mammals of the species to which said test animal belongs.

2. A process according to claim 1 wherein said biological material is removed from said test animal before macroscopically visible tumors are present in said test animal.

3. A process according to claim 1 wherein said biological material is removed from said test animal at least 4 days after the first administration of said material to said test animal.

4. A process according to claim 1 wherein said test animal is a mammal.

5. A process according to claim 4 wherein said test animal is a rat.

6. A process according to claim 1 wherein said material is administered to said test animal orally, intraperitoneally or by inhalation.

7. A process according to claim 1 wherein said biological material comprises blood, or a blood fraction other than serum, from said test animal.

8. A process according to claim 7 wherein said biological material comprises plasma from said test animal.

9. A process according to claim 1 wherein said assay is effected by contacting said biological material with antibodies to said phosphoprotein, said antibodies not being capable of forming a conjugate with the 25K protein fraction from human plasma nor the 35K protein fraction from rat plasma, and detecting the presence of a reaction product formed between said antibodies and said phosphoprotein.

10. A process according to claim 9 wherein the presence of said reaction product is determined by ELISA assay.

11. A process according to claim 9 wherein the presence of the reaction product is determined by radioimmunoassay.

12. A process according to claim 9 wherein said antibodies are monoclonal antibodies.

13. A process according to claim 9 wherein said antibodies are derived from an animal immunized with said phosphoprotein, said immunized animal being of the same species as said test animal.

14. A process for determining the ability of a material to induce cancer in a test animal, said process comprising:
   administering said material to said test animal;
   at least 4 days after the first administration of said material to said test animal but before cancerous tumors are observable in said test animal, withdrawing blood from said test animal;
   preparing plasma from said blood;
   assaying said plasma for the presence of a phosphoprotein having the following characteristics:
   (a) not being precipitated by 30% saturated aqueous ammonium sulfate solution at 25° C.;
   (b) having a molecular weight of approximately 60,000;
   (c) being precipitated from aqueous solution by 3.3% streptomycin sulfate;
   (d) having substantially no autophosphorylation activity but being phosphorylated with adenosine triphosphate in the presence of an exogenous protein kinase;
   (e) having substantially no protein kinase activity;
   (f) having the capacity to liberate ribonucleic acid from cell nuclei; and
   (g) not being present in the maternal blood of non-cancerous normal pregnant mammals of the species to which said test animal belongs;
   said assay being effected by contacting said plasma with antibodies to said phosphoprotein, said antibodies not being capable of forming a conjugate with the 25K protein fraction from human plasma nor the 35K protein fraction from rat plasma; and detecting the presence of a reaction product formed between said antibodies and said phosphoprotein.

15. A process according to claim 14 wherein the presence of said reaction product is determined by ELISA assay.

16. A process according to claim 14 wherein the presence of said reaction product is determined by radioimmunoassay.

17. A process accoarding to claim 14 wherein said test animal is a mammal.

18. A process according to claim 17 wherein said test animal is a rat.

19. A process for determining the presence of cancer-inducing factors in an environment, said process comprising exposing a test animal to said environment and thereafter assaying biological material from said test animal for the presence of a phosphoprotein having the following characteristics:
   (a) not being precipitated by 30% saturated aqueous ammonium sulfate solution at 25° C.;
   (b) having a molecular weight of approximately 60,000;
   (c) being precipitated from aqueous solution by 3.3% streptomycin sulfate;
   (d) having substantially no autophosphorylation activity but being phosphorylated with adenosine triphosphate in the presence of an exogenous protein kinase;
   (e) having substantially no protein kinase activity;
   (f) having the capacity to liberate ribonucleic acid from cell nuclei; and
   (g) not being present in the maternal blood of non-cancerous normal pregnant mammals of the species to which said test animal belongs.

* * * * *